United States Patent [19]

Horiguchi et al.

[11] Patent Number: 5,328,456
[45] Date of Patent: Jul. 12, 1994

[54] IRRIGATION AND ASPIRATION APPARATUS

[75] Inventors: Masayuki Horiguchi, Ichinomiya; Hideo Oda, Gamagori, both of Japan

[73] Assignee: Nidek Co., Ltd., Aichi, Japan

[21] Appl. No.: 51,292

[22] Filed: Apr. 23, 1993

Related U.S. Application Data

[63] Continuation of Ser. No. 789,498, Nov. 8, 1991, abandoned.

[30] Foreign Application Priority Data

Nov. 13, 1990 [JP] Japan ................... 2-306434

[51] Int. Cl.⁵ .......................................... A61B 17/20
[52] U.S. Cl. .............................. 604/22; 604/30; 601/2
[58] Field of Search ....................... 604/22, 30; 606/169–171; 128/24 AA

[56] References Cited

U.S. PATENT DOCUMENTS

| | | | |
|---|---|---|---|
| 3,124,162 | 3/1964 | Cameron | 137/625.46 |
| 3,542,071 | 11/1970 | Lightner et al. | 137/625.46 |
| 3,590,872 | 7/1971 | Baity | 137/625.46 |
| 3,812,855 | 5/1974 | Banko | 128/24 AA |
| 3,902,495 | 9/1975 | Weiss et al. | 128/24 AA |
| 4,195,631 | 4/1980 | Baucom | 137/625.46 |
| 4,274,411 | 6/1981 | Dotson, Jr. | 604/30 |
| 4,299,221 | 11/1981 | Phillips et al. | 604/30 |
| 4,576,199 | 3/1986 | Suensson et al. | 604/905 |
| 4,705,038 | 11/1987 | Sjostrom et al. | 604/22 |
| 4,747,820 | 5/1988 | Hornlein et al. | 128/24 AA |
| 4,933,843 | 6/1990 | Scheller et al. | 604/22 |
| 4,935,005 | 6/1990 | Haines | 604/30 |
| 5,154,696 | 10/1992 | Shearing | 604/22 |

Primary Examiner—C. Fred Rosenbaum
Assistant Examiner—Michael Rafa
Attorney, Agent, or Firm—Nikaido, Marmelstein, Murray & Oram

[57] ABSTRACT

An irrigation and aspiration apparatus for cataract surgery or the like, which is particularly suitable for aspiration and removal of the cortex lentis during the surgical operation. As for the structure, the irrigation and aspiration apparatus of the present application includes a selector coupling to which ends of a plurality of aspiration tubes are connected, while the other ends of the aspiration tubes are respectively connected to handpieces which can perform aspiration, so that one of the handpieces for aspirating irrigating fluid and the like from a diseased eye of a patient can be chosen by switching the selector coupling. With this structure, aspiration and removal of the residual cortex after removal of the lens nucleus in the surgery of the crystalline lens can be accomplished easily and reliably, thereby relieving the doctor and the patient from the stress and load of the surgical operation.

5 Claims, 5 Drawing Sheets

IRRIGATION AND ASPIRATION APPARATUS

This application is a continuation of application Ser. No. 07/789,498 filed Nov. 8, 1991, now abandoned.

FIELD OF THE INVENTION

The present invention relates to an irrigation and aspiration apparatus for cataract surgery and, more particularly, to an apparatus suitable for aspiration and removal of the cortex lentis.

DESCRIPTION OF THE PRIOR ART

Background of the Invention

In the field of ophthalmology, there has been known an irrigation and aspiration apparatus for removing, out of an eye, the residual cortex lentis after removal of the lens nucleus, and tissue particles emulsified by an ultrasonic probe in a method called the phacoemulsification. More specifically, it is an apparatus by which irrigating fluid is supplied to a patient's eye, and the cortex and tissue particles, along with the irrigating fluid, are discharged out of the eye while controlling the suction pressure to be maintained within a predetermined range. Conventionally, only one type of handpiece for irrigation and aspiration is connected to this kind of apparatus, and the operator inevitably needs to use this only one handpiece (aspiration port) to aspirate and remove all the residual cortex in the lens capsule, or to reconnect a different handpiece to the apparatus. Furthermore, in case of using two handpieces for irrigation-aspiration and phacoemulsification, it is necessary to reconnect each handpiece to an irrigation tube and an aspiration tube.

Such a conventional apparatus involves the following problems taking an example of aspirating and removing the cortex lentis. FIGS. 6A and 6B are simplified explanatory views illustrating a method of surgical operation for removing the residual cortex lentis. The operator stands on the head top side of a patient's eye. (Hereinafter, this position will be expressed as the "twelve-o'clock position", and positions at angles of 90, 180 and 270 degrees clockwise from here are respectively referred to as the "three-, six- and nine-o'clock positions".) Usually, as shown in the drawings, a portion of the patient's eye in the twelve-o'clock position is incised, and from this incision, the handpiece for irrigation and aspiration is inserted into the lens capsule so as to perform the surgical operation. As clearly understood from the drawings, however, it is extremely difficult to aspirate and remove the residual cortex within the capsule in the twelve-o'clock position in the vicinity of the incision because the iris and the anterior capsule become obstacles. Unless the cortex of the anterior capsule is completely aspirated, it is highly probable that the anterior capsular opacification will be caused after the surgery. Taking the post-operative progress into consideration, it is unfavorable to form another incision for inserting the handpiece in the three-, six- or nine-o'clock position. Then, if the distal end of the aspiration port is forcibly approached toward the capsule in the twelve-o'clock position, there is a risk that the incision and the corneal endothelium will be damaged. Further, due to such operational difficulty, time for the operation will be extended, resulting in a problem that the operator and the patient will be fatigued to an increased degree.

It is therefore an object of the present invention to provide an apparatus by which aspiration and removal of the residual cortex after a surgery of the crystalline lens, or particularly, removal of the lens nucleus in cataract surgery, can be accomplished easily and reliably, thereby relieving the doctor and the patient from the stress and load of the surgical operation.

SUMMARY OF THE INVENTION

In order to achieve the above-described object, the irrigation and aspiration apparatus according to the present invention has the following structure.

An irrigation and aspiration apparatus by which irrigating fluid is infused into a diseased eye of a patient and the infused irrigating fluid with the residual cortex and the like is discharged out of the eye, characterized in that ends of a plurality of aspiration tubes are connected to handpieces which can perform aspiration, and that the other ends of the aspiration tubes are connected to a selector coupling, so that one of the handpieces can be chosen for aspiration by switching the selector coupling.

The handpieces described above are characterized in that they are handpieces for irrigation and aspiration and handpieces exclusively used for aspiration.

The handpieces exclusively used for aspiration described above are characterized in that each of them is provided with a tip having a small diameter.

The selector coupling described above is characterized in that it comprises a block having a plurality of through holes and a block having one through hole, which blocks are relatively slidable to change the aspiration course, so that the aspiration courses within the selector coupling are substantially straight.

The selector coupling described above is characterized in that it is located between the handpieces and a connector with a suction pressure control system, the suction pressure control system being operated commonly for the handpieces.

DETAILED DESCRIPTION OF THE INVENTION

One embodiment of the present invention will be hereinafter described with reference to the attached drawings.

Figure 1:
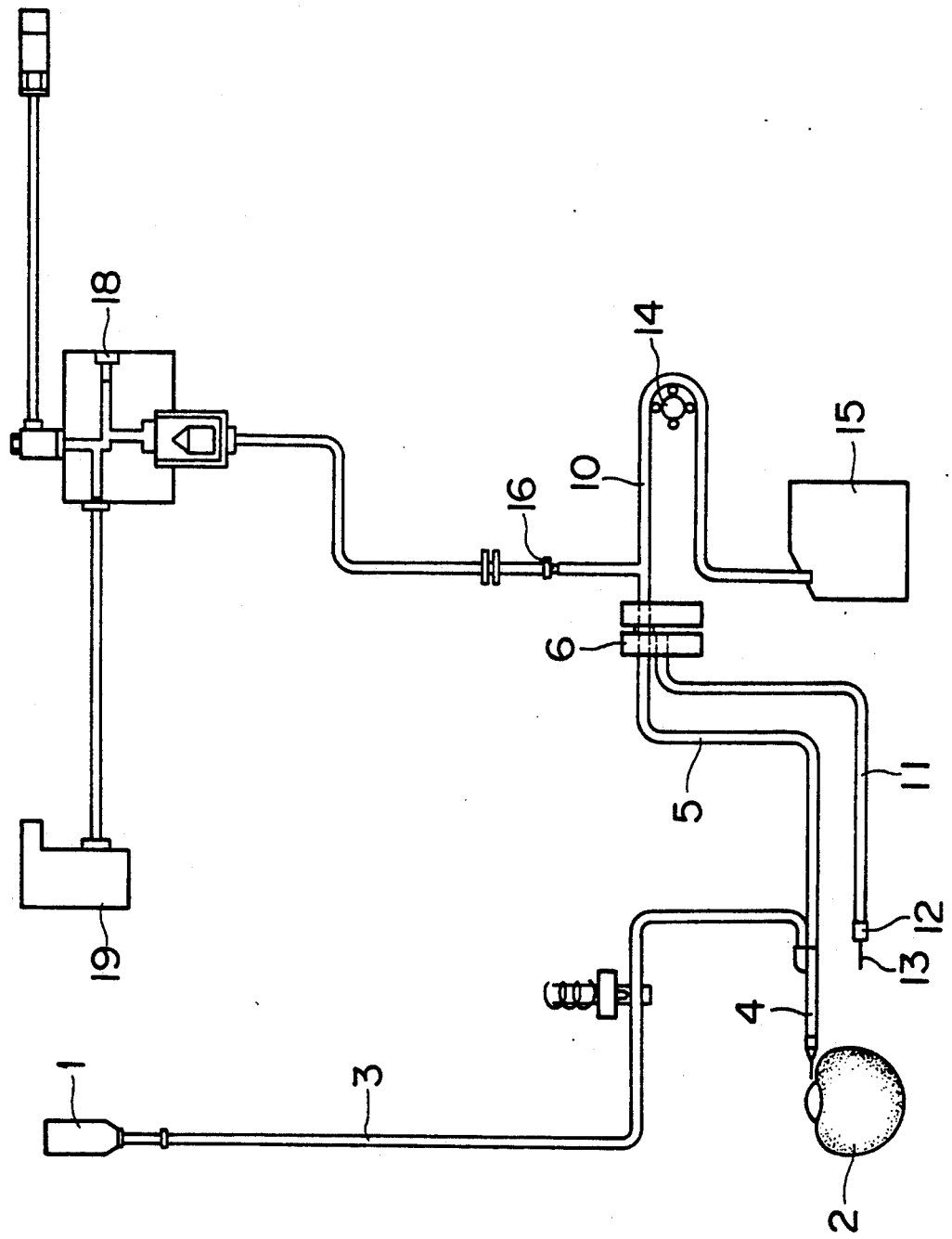
FIG. 1 is an explanatory view illustrating the entire structure of an irrigation and aspiration apparatus according to one embodiment of the present invention.

FIG. 1 is an explanatory view illustrating the entire structure of an irrigation and aspiration apparatus according to the embodiment.

Reference numeral 1 denotes an irrigating bottle containing irrigating fluid such as physiological saline solution, and this irrigating bottle is placed at a level suitable for controlling the irrigation pressure to be infused into a patient's eye 2. Numeral 3 denotes an irrigation tube for supplying the irrigating fluid delivered from the irrigating bottle 1, and the other end of this irrigation tube is connected to an I/A (Irrigation/Aspiration) handpiece 4. The I/A handpiece 4 is designed in such a manner that the irrigating fluid is infused into the patient's eye 2 from a peripheral distal end portion thereof, and that the residual cortex, together with the irrigating fluid, is aspirated through a tip including an aspiration port which is fixed on the distal end of the handpiece.

Figure 2:
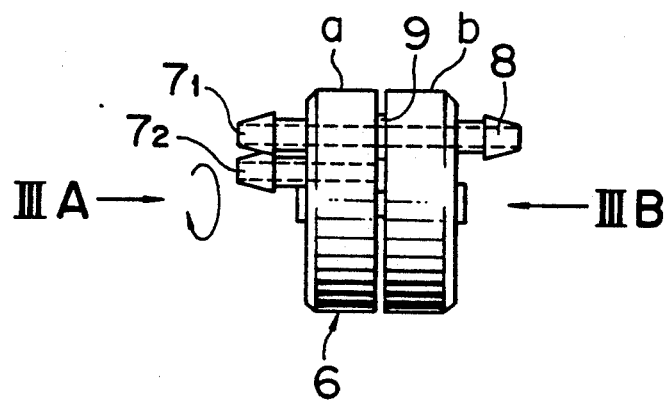
FIG. 2 is a side view of a selector coupling in FIG. 1.
Figure 3A:
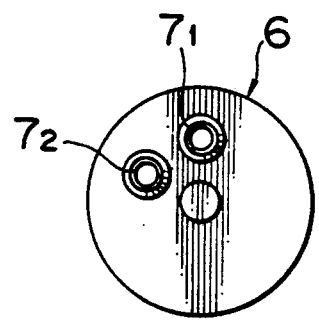
FIG. 3A is a view of the selector coupling, as viewed in a direction indicated by the arrow IIIA of FIG. 2.
Figure 3B:
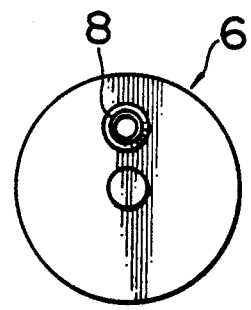
FIG. 3B is a view of the selector coupling, as viewed in a direction indicated by the arrow IIIB of FIG. 2.

Reference numeral 5 designates an aspiration tube for discharging the irrigating fluid and the residual cortex which are sucked through the I/A handpiece 4. Numeral 6 designates a selector coupling which is connected to the aspiration tube 5, and this selector coupling is illustrated in an enlarged view of FIG. 2. FIG. 3A is a view showing a portion a of the selector coupling 6, as viewed in a direction indicated by the arrow IIIA of FIG. 2, and FIG. 3B is a view showing a portion b of the selector coupling 6, as viewed in a direction indicated by the arrow IIIB of FIG. 2. In the portion a shown in FIG. 3A, two nipples $7_1$ and $7_2$ are provided at the same distance from the center axis of the selector coupling 6. A hole having substantially the same diameter as the aspiration tube 5 is formed in each of these nipples, and it is also extended through the portion a. A nipple 8 is provided in the portion b shown in FIG. 3B, and a hole having substantially the same diameter as the aspiration tube 5 is formed in this nipple and extended through the portion b in a manner similar to the arrangement shown in FIG. 3A.

The portion a of the selector coupling 6 can be rotated about its center axis, relatively to the portion b, in a direction indicated by the arrow of FIG. 2. When the portion a of the selector coupling 6 is rotated, either connection between the holes of the nipples $7_1$ and 8 or connection between the holes of the nipples $7_2$ and 8 can be selected. The portion a or b includes stoppers enabling the accurate positioning of the nipples at communication positions, so that the operator can readily perceive these positions. In place of such stoppers, alignment marks or the like may be put on the portions a and b. Besides, instead of rotating the portions a and b, for instance, they may be arranged to be simply slidable.

In order to flow the irrigating fluid and the like from the through hole of the nipple $7_1$ or $7_2$ into the through hole within the portion b, an O-ring 9 is provided on the side of the portion b which faces the portion a so that, even when the portions a and b are relatively rotated to change the irrigation course, the irrigating fluid and the like will not leak to the outside.

The aspiration tube 5 is connected through the nipple $7_1$ to the selector coupling 6, and the irrigating fluid and the like flowing in the aspiration tube 5 passes through the selector coupling 6, and is supplied to an aspiration tube 10.

Further, the selector coupling 6 is connected, through the nipple $7_2$, to an aspiration tube 11. The aspiration tube 11 is connected with an aspiration handpiece 12. The irrigating fluid and the like is aspirated through a thin tip 13 including an aspiration port which is fixed to the handpiece 12, and such aspirated fluid is discharged via the selector coupling 6 to the aspiration tube 10.

Figure 4:
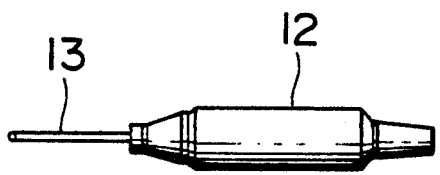
FIG. 4 is a view showing an appearance of a thin tip of a standard type including an aspiration port which is fixed to a handpiece.

The thin tip 13 is a small-diameter tip to be exclusively used for aspiration operation so that it can be inserted even into an incision of a small diameter. FIG. 4 shows an appearance of the thin tip 13 of a standard type including the aspiration port which is fixed to the handpiece 12.

For cataract surgery, especially for phacoemulsification, there is a method in which only one tip is inserted into the crystalline lens of the patient, and there is another method in which a lens spatula for supporting the lens nucleus, as well as the tip, is inserted into the lens. In the latter method, a second incision (side port) is usually formed in the nine-o'clock position when the eye to be operated is a right eye of the patient and in the three-o'clock position when the eye to be operated is a left eye of the patient. This side port has a small width of about 1 mm, and there is no leakage of aqueous humor or the like even if the side port is not sutured after the surgery. Therefore, the side port does not particularly influence the postoperative progress of the patient's eye. The cortex in the twelve-o'clock position, which is difficult to aspirate from the first incision, can be easily aspirated and removed by the thin tip 13 inserted through the side port.

Figure 5:
FIG. 5 is a view showing an appearance of an improved thin tip which is curved.
Figure 6A:
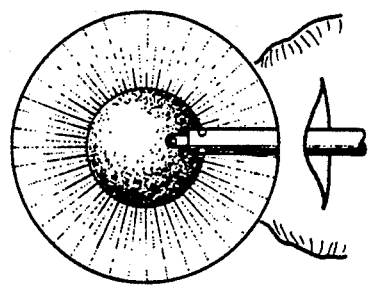
FIGS. 6A and 6B are simplified explanatory views illustrating a method of surgical operation for removing the residual cortex lentis.
Figure 6B:
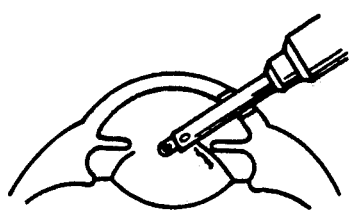

FIG. 5 shows an appearance of an improved thin tip which is curved. Since the thin tip is inserted from the three-o'clock position or nine-o'clock position to remove the cortex in the twelve-o'clock position, as described above, it is preferable in improving the operational efficiency to curve the thin tip at an appropriate angle.

Reference numeral 14 denotes a pump to produce a suction pressure, and 15 denotes a waste bag in which the aspirated irrigating fluid and cortex is contained.

In order to protect the lens capsule, the irrigation and aspiration apparatus is provided with a suction pressure control system for controlling the pressure within the lens capsule.

A connector 16 is provided on a portion of the aspiration tube 10, and the suction pressure control system is connected with the apparatus through the connector 16.

The suction pressure control system comprises a pressure sensor 18, an electromagnetic valve 19 and the like. The suction pressure is constantly detected by the pressure sensor 18, and when the suction pressure is excessively raised, the electromagnetic valve 19 is opened to let the air in, thereby decreasing the suction pressure.

With the apparatus according to the above-described embodiment, the operation will be roughly described below.

There are various operation methods. In one method, for example, the corneosclera in the twelve-o'clock position is incised; the lens nucleus is aspirated out of the capsule; and a side port is formed in the three-o'clock position, proceeding to aspirating the residual cortex lentis.

The selector coupling 6 is set in a state for communicating the aspiration tubes 5 and 10, and the plug of the irrigating bottle 1 is opened to flow the irrigating fluid into the crystalline lens at a constant velocity. The suction pressure, which is generated by the pump 14, is transmitted through the aspiration tube 10, the selector coupling 6 and the aspiration tube 5 to the I/A handpiece 4. The residual cortex after the lens nucleus removal in the cataract surgery is aspirated and removed through the aspiration port of the tip attached to the distal end of the I/A handpiece 4, and it is discharged through the aspiration tube 5, the selector coupling 6 and the aspiration tube 10 into the waste bag 15. During this operation, the suction pressure is detected by the pressure sensor 18, and the electromagnetic valve 19 is operated so that the suction pressure is regulated and maintained within a predetermined range. Such control is performed under the command of a microcomputer (not shown) of the apparatus.

After the residual cortex has been completely removed except in the twelve-o'clock position, the portion a of the selector coupling 6 is rotated relatively to the portion b, thus communicating the aspiration tubes 11 and 10. When the aspiration course is changed in this manner, the suction pressure is transmitted through the aspiration tube 11 to the distal end of the thin tip 13 attached to the aspiration handpiece 12.

The thin tip 13 of the aspiration handpiece 12 is inserted from the side port so as to aspirate and remove the residual cortex of the anterior capsule in the twelve-o'clock position in the vicinity of the incision.

The above description is based on the so-called phacoemulsification. The selector coupling of the embodiment is suitable for this operation method because aspiration courses within the selector coupling are substantially straight, and because the through holes of the nipples are formed to have substantially the same diameter as the aspiration tubes, so that the courses within the coupling will not be clogged even when tissue pieces of the lens nucleus are aspirated.

Needless to say, this apparatus can be used as an irrigation and aspiration apparatus for other methods such as planned extracapsular lens extraction.

When a probe for phacoemulsification is not connected to the apparatus, the aspirated tissues are fluid and extremely small, so that a forked coupling which can be selectively closed may be used as a selector coupling.

The selector coupling in the above embodiment serves as a selector between the I/A handpiece for irrigation and aspiration and the handpiece for only aspiration. Further, as the selector coupling is provided with through holes for selecting irrigation courses, the selector coupling can be used for selecting between the different kinds of the I/A handpieces, between the same kind I/A handpieces (one is for a spare) and between two handpieces for irrigation-aspiration and for phacoemulsification.

Figure 7:
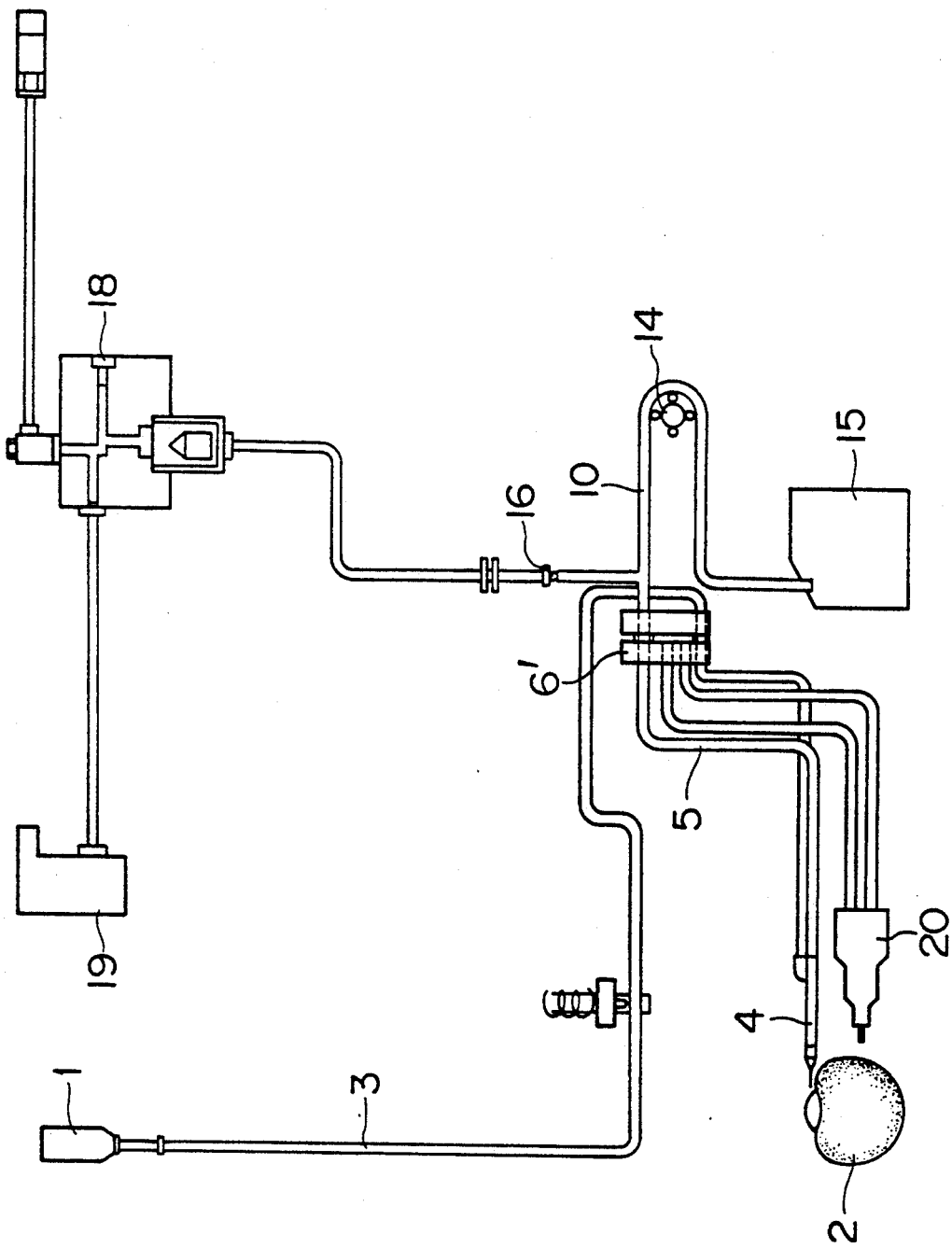
FIG. 7 is an explanatory view illustrating the entire structure of an irrigation and aspiration apparatus according to another embodiment of the present invention.

FIG. 7 is an explanatory view of using the selector coupling according to the invention as a selector between two handpieces for irrigation-aspiration and for phacoemulsification. In the figure, like reference numerals are applied to like members as in FIG. 1. Reference numeral 20 denotes a handpiece for phacoemulsification.

Figure 8:
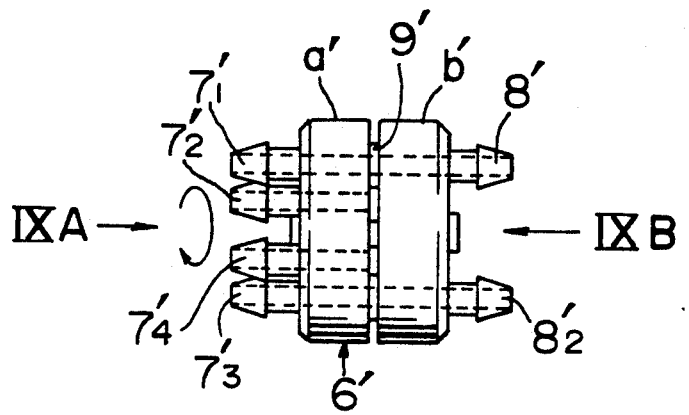
FIG. 8 is a side view of a selector coupling in FIG. 7.
Figure 9A:
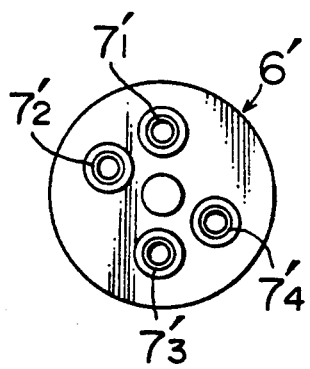
FIG. 9A is a view of the selector coupling, as viewed in a direction indicated by the arrow IXA of FIG. 8.

Reference numeral 6' denotes a selector coupling used in another embodiment according to the invention. As seen from FIGS. 8 and 9A, the portion a' of the selector coupling 6' is provided with each of nipples $7_3'$ and $7_4'$ for irrigation on one of the opposite positions of the nipples $7_1'$ and $7_2'$, respectively. Each of the nipples $7_3'$ and $7_4'$ is provided with a hole having substantially the same diameter as the irrigation tube.

Figure 9B:
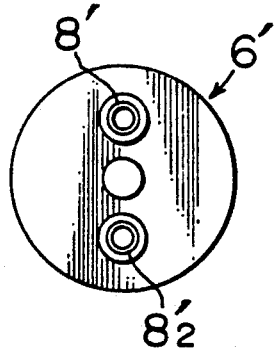
FIG. 9B is a view of the selector coupling, as viewed in a direction indicated by the arrow IXB of FIG. 8.

Further, as illustrated in FIG. 9B, the portion b' of the selector coupling 6' is provided with a nipple $8_2'$ on the opposite position of the nipple 8'.

In using the apparatus, as illustrated in FIG. 7, the irrigation tube 3 is connected to the nipple $8_2'$, and the aspiration tube 10 is connected to the nipple 8'. Each of the aspiration tube 5 and the irrigation tube of the I/A handpiece is connected to one of the nipples $7_1'$ and $7_3'$, respectively. Further, each of the aspiration tube and the irrigation tube of the handpiece for phacoemulsification is connected to one of the nipples $7_2'$ and $7_4'$, respectively. Thus, the operator can select between two handpieces for irrigation-aspiration and for phacoemulsification due to revolution of the selector coupling 6'.

According to the present invention, surgery of the crystalline lens, or particularly, aspiration and removal of the residual cortex after removal of the lens nucleus in cataract surgery can be accomplished easily and reliably, thereby relieving the doctor and the patient from the stress and load of the surgical operation.

What is claimed is:

1. An irrigation and aspiration apparatus for ophthalmic use comprising:
   an irrigation fluid source capable of adjusting a flow;
   an irrigation handpiece connected with said fluid source through an irrigation tube and infusing an irrigation fluid into a patient's eye;
   plural aspiration handpieces for aspirating a waste fluid in the patient's eye, one of said aspiration handpieces sharing one handpiece with said irrigation handpiece by being provided with aspirating means;
   a selector coupling having plural inlets and one outlet and said selector coupling selecting one of the plural aspiration handpieces by changing an inlet's position into a position communicated straight with said outlet, said plural inlets being connected with aspiration tubes connected with said aspiration handpieces, and said outlet being connected with a second aspiration tube leading waste fluid to a predetermined place; and
   means for generating irrigating pressure, which irrigates the waste fluid in the patient's eye.

2. An irrigation and aspiration apparatus according to claim 1, wherein each of said handpieces exclusively used for aspiration is provided with a tip having a small diameter.

3. An irrigation and aspiration apparatus according to claim 1, wherein said selector coupling comprises a first block having a plurality of through holes and a second block having one through hole, said first and second blocks are relatively slidable to change aspiration courses, so that the aspiration courses within said selector coupling are substantially straight.

4. An irrigation and aspiration apparatus according to claim 1, wherein said selector coupling comprises a first block having a plurality of through holes and a second block having one through hole, said first and second blocks are relatively rotated to change the aspiration courses, so that the aspiration courses within said selector coupling are substantially straight.

5. An irrigation and aspiration apparatus according to claim 1, wherein said selector coupling is located between said handpieces and a connector with a suction pressure control system, said suction pressure control system being operated commonly for said handpieces.

* * * * *